(12) United States Patent
Farbos

(10) Patent No.: US 7,435,227 B2
(45) Date of Patent: Oct. 14, 2008

(54) METHOD AND APPARATUS FOR GENERATING AN INDICATION OF A LEVEL OF VIGILANCE OF AN INDIVIDUAL

(75) Inventor: Bruno Farbos, Montreal (CA)

(73) Assignee: Biocognisafe (BCS) Technologies, Dorval, Quebec (CA)

( * ) Notice: Subject to any disclaimer, the term of this patent is extended or adjusted under 35 U.S.C. 154(b) by 156 days.

(21) Appl. No.: 10/938,663

(22) Filed: Sep. 13, 2004

(65) Prior Publication Data

US 2006/0055546 A1    Mar. 16, 2006

(51) Int. Cl.
*A61B 13/00* (2006.01)
*G08B 23/00* (2006.01)
(52) U.S. Cl. ................. 600/558; 340/575; 340/576
(58) Field of Classification Search ............... 600/558; 340/575–576
See application file for complete search history.

(56) References Cited

U.S. PATENT DOCUMENTS

| | | | | |
|---|---|---|---|---|
| 5,008,946 A | * | 4/1991 | Ando | 382/104 |
| 5,360,971 A | * | 11/1994 | Kaufman et al. | 250/221 |
| 5,570,698 A | * | 11/1996 | Liang et al. | 600/558 |
| 5,795,306 A | * | 8/1998 | Shimotani et al. | 600/558 |
| 5,805,720 A | * | 9/1998 | Suenaga et al. | 382/117 |
| 5,892,837 A | * | 4/1999 | Luo et al. | 382/117 |
| 6,070,098 A | * | 5/2000 | Moore-Ede et al. | 600/544 |
| 6,072,893 A | * | 6/2000 | Luo et al. | 382/117 |
| 6,542,081 B2 | | 4/2003 | Torch | |
| 6,927,694 B1 | * | 8/2005 | Smith et al. | 340/576 |
| 7,011,410 B2 | * | 3/2006 | Bolger et al. | 351/209 |
| 7,027,621 B1 | * | 4/2006 | Prokoski | 382/118 |
| 2002/0188219 A1 | | 12/2002 | Suchard | |

FOREIGN PATENT DOCUMENTS

| | | |
|---|---|---|
| WO | 9918843 | 4/1999 |
| WO | 0174236 | 10/2001 |

OTHER PUBLICATIONS

Wingate et al. Automated Pupil Size Determination for Evaluating Fluctuations in Physiological Arousal. Signal Processing Proceedings, 1998. ICSP '98, vol. 2, Oct. 12-16, 1998 pp. 1666-1669 vol. 2 p. 1667.
Santamaria and Chiappa "The EEG of Drowsiness in Normal Adults" Journal of Clinical Neurophysiology, 4, 4, 1987, pp. 327-379.
Level 0.5" by Wright in "Vigilance on the civil flight deck: incidence of sleepiness and sleep during long-haul flights and associated changes in physiological parameters" Ergonomics, 44, 1, 82 (25p).
"Lips and face real time tracker", Conference on computer vision and pattern recognition, by Olivier, Pentland and Berard in Puerto Rico, Jun. 1997, pp. 123-129.
"A new method for describing search patterns and quantifying visual load using eye movement data" by Chia-Fen Chi and Fang-Tsan Lin, International Journal of Industrial Ergonomics 19 (1997) 249-257.

* cited by examiner

*Primary Examiner*—Max Hindenburg
*Assistant Examiner*—Jeffrey G Hoekstra
(74) *Attorney, Agent, or Firm*—Ogilvy Renault LLP

(57) ABSTRACT

A method and apparatus are disclosed for generating an indication of a level of vigilance of an individual using a gaze acquisition unit providing a gaze data stream of at least one eye of the individual, a processing unit receiving the gaze data stream and determining a level of vigilance.

10 Claims, 5 Drawing Sheets

METHOD AND APPARATUS FOR GENERATING AN INDICATION OF A LEVEL OF VIGILANCE OF AN INDIVIDUAL

CROSS-REFERENCE TO RELATED APPLICATIONS

This is the first application filed for the present invention.

TECHNICAL FIELD

This invention relates to the field of cognitive systems. More precisely, this invention pertains to the field of detecting a level of vigilance of an individual.

BACKGROUND OF THE INVENTION

Despite the advancement of science and technology, humans are still required to achieve complex tasks in which small errors may be very costly. Errors may occur for instance due to fatigue/drowsiness. In the case of a moving vessel such as a truck, the outcome of such errors may be tragic.

It is known to detect drowsiness using various methods. For instance, in the PERCLOS (PERcent eyelid CLOSure) method, a measure of the percentage of eyelid closure over the pupil over time is performed and reflects slow eyelid closures rather than blinks. Unfortunately, such detecting is often of limited interest since, at this point, it is too late to implement an alternative strategy and the situation may already be critical. There is therefore a need for a method and apparatus which enable a prediction of drowsiness.

In another prior art method an EEG (Electroencephalogram) is used to measure signal components over 30 Hz which are known to have a correlation with a subject's drowsiness. Unfortunately such method is cumbersome.

There is a need for a method and apparatus that will overcome at least one of the above-identified drawbacks.

SUMMARY OF THE INVENTION

It is an object of the invention to provide a method apparatus for generating an indication of a level of vigilance of an individual.

It is another object of the invention to provide a method and apparatus for alerting an individual in the case of a decrease of a level of vigilance of the individual.

It is another object of the invention to provide a method and apparatus for predicting drowsiness of an individual.

According to a first aspect of the invention, there is provided an apparatus for generating an indication of a level of vigilance of an individual, the apparatus comprising a gaze acquisition unit providing a gaze data stream of at least one eye of the individual, a processing unit receiving the gaze data stream and using the gaze data stream to determine the indication of the level of vigilance and a data providing unit receiving and providing the indication of the level of vigilance.

According to another aspect of the invention, there is provided a method for generating an indication of a level of vigilance of an individual, the method comprising acquiring a plurality of gaze directions of the individual, analyzing the acquired plurality of gaze directions of the individual to determine a gaze pattern and generating an indication of the level of vigilance using the gaze pattern.

According to another aspect of the invention, there is provided a method for predicting drowsiness of an individual, the method comprising acquiring a plurality of gaze directions of the individual, analyzing the acquired plurality of gaze directions of the individual to determine a gaze pattern, generating an indication of the level of vigilance using the gaze pattern and providing an indication of drowsiness of the individual using the indication of said level of vigilance.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION OF THE PREFERRED EMBODIMENT

The definition of drowsiness (also referred to as sleepiness) may be found in Santamaria and Chiappa "The EEG of Drowsiness in Normal Adults" Journal of Clinical Neurophysiology", 4, 4, 1987, pp 327-379, hereby incorporated by reference. Sleepiness is also referred to as "level 0.5" by Wright in "Vigilance on the civil flight deck: Incidence of sleepiness and sleep during long-haul flights and associated changes in physiological parameters" Ergonomics, 44, 1, 82 (25p), hereby incorporated by reference. While each of the two last references discloses a definition of sleepiness, it should be understood that the definition of "sleepiness" should not be limited to these definitions and the skilled addressee will appreciate that other definitions of sleepiness may be found in the pertinent literature. This description is intended to encompass all such definitions.

Figure 1:
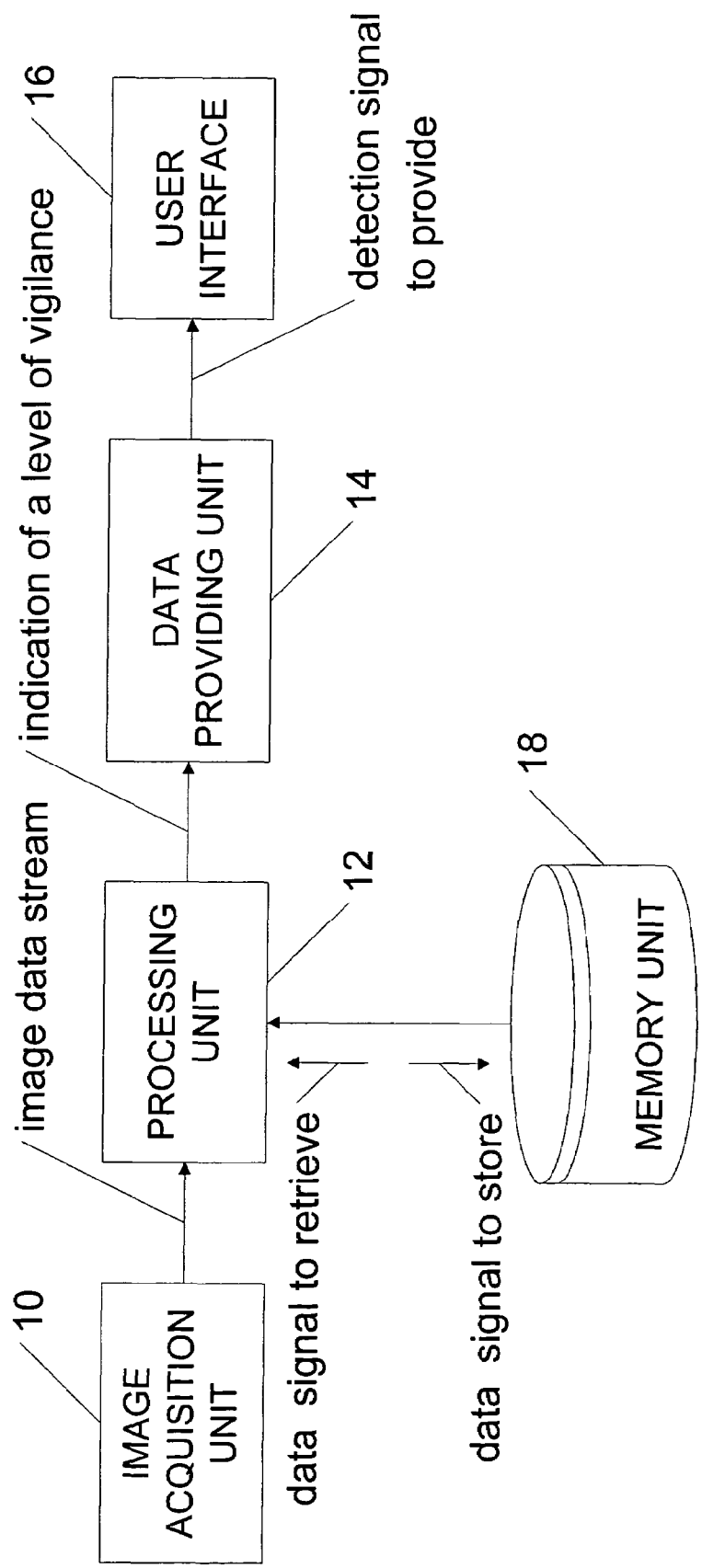
FIG. 1 is a block diagram showing an embodiment of an apparatus which uses an indication of a level of vigilance of an individual.

Now referring to FIG. 1, there is shown an embodiment of an apparatus 8 which uses an indication of a level of vigilance of an individual.

The apparatus 8 comprises an image acquisition unit 10 which is an embodiment of a gaze acquisition unit, a processing unit 12, a data providing unit 14, a user interface 16 and a memory unit 18.

The image acquisition unit 10 is adapted to provide an image data stream signal which is an embodiment of a gaze data stream. The image data stream signal comprises a plurality of timely-spaced images of an individual. More precisely, the timely-spaced images comprises at least the eyes of the individual. It has been contemplated that the timely-spaced images may comprise images of only one of the eyes of the individual. It will be appreciated that preferably the image acquisition unit 10 is a digital black and white image acquisition unit further having infra-red sensors in order to detect the eyes of the individual by day or night. The image acquisition unit 10 preferably provides a resulting image which results from the subtraction of a bright image from a dark image.

The processing unit 12 is adapted to provide an indication of a level of vigilance of the individual using the image data stream signal provided by the image acquisition unit 10 and further using a data signal to retrieve provided by the memory unit 18. The processing unit 12 is further adapted to provide a data signal to store to the memory unit 18. The processing unit 12 is selected from the group consisting of field programmable gate arrays (FPGA), processors, microcontrollers, dedicated circuits or the like.

The data providing unit 14 receives the indication of a level of vigilance and provides a detection signal to provide to the user interface 16.

The user interface 16 is adapted to provide a signal to an individual (or to another entity as discussed below) according to the detection signal to provide to the user interface 16. The signal may be a sensorial data which is selected from a group consisting of visual signals, acoustic signals, stimulation signals and motion signals. The user interface 16 may therefore comprise for instance a sound providing unit, a display unit, a motion providing unit, a cell phone, etc. The skilled addressee will appreciate that existing user interfaces providing information to the individual such as LCD screen display in car, car navigation console, etc may be advantageously used in order to provide the signal to the individual.

The memory unit 18 is adapted for storing a data signal to store and further to provide the data signal to retrieve as explained below.

Figure 2:
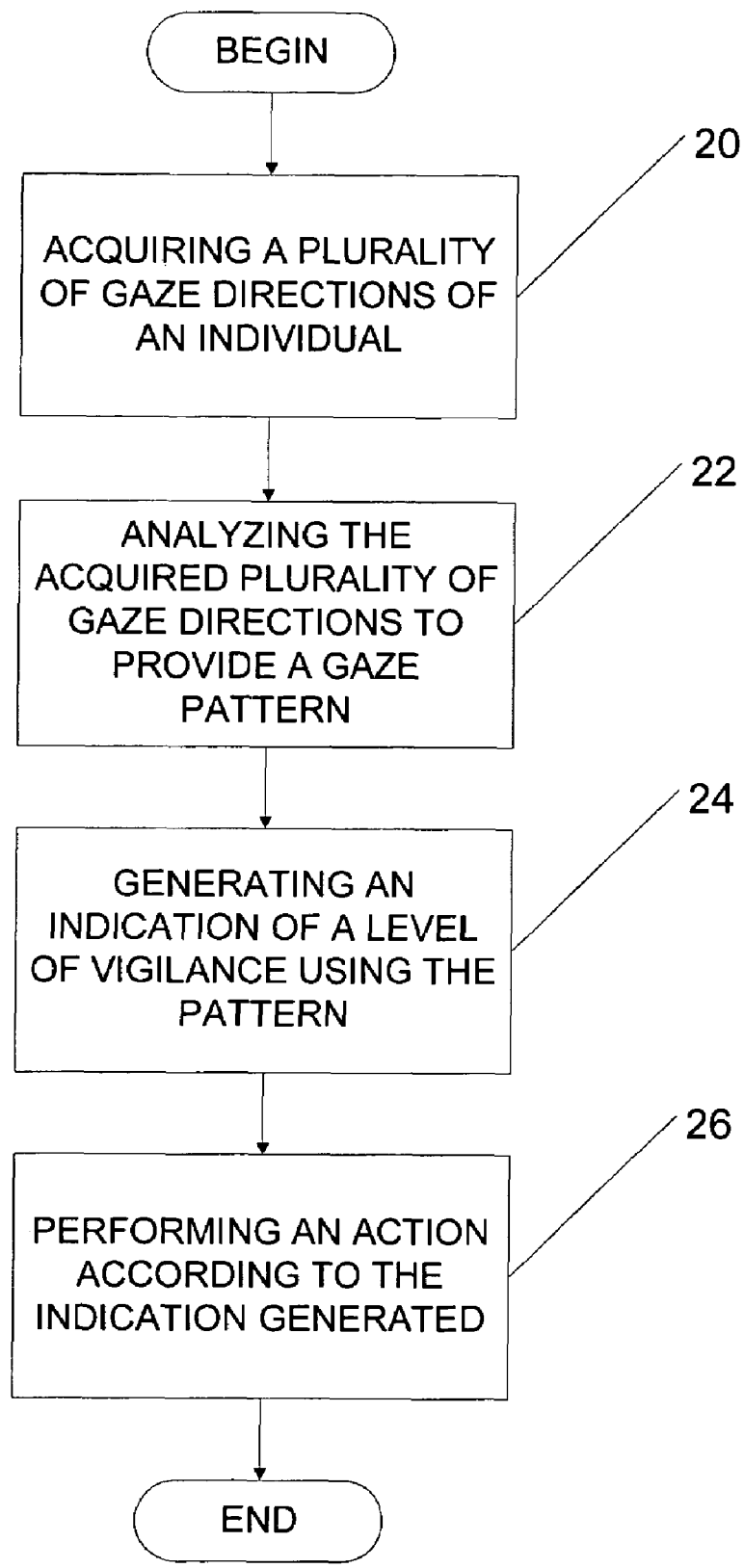
FIG. 2 is a flowchart showing an embodiment wherein an action is performed according to an indication of a level of vigilance.

Referring to FIG. 2, there is shown how an action is performed according to a generated indication of a level of vigilance.

According to step 20, a plurality of gaze directions of the individual is acquired. The plurality of gaze directions is acquired using the image acquisition unit 10.

Figure 3:
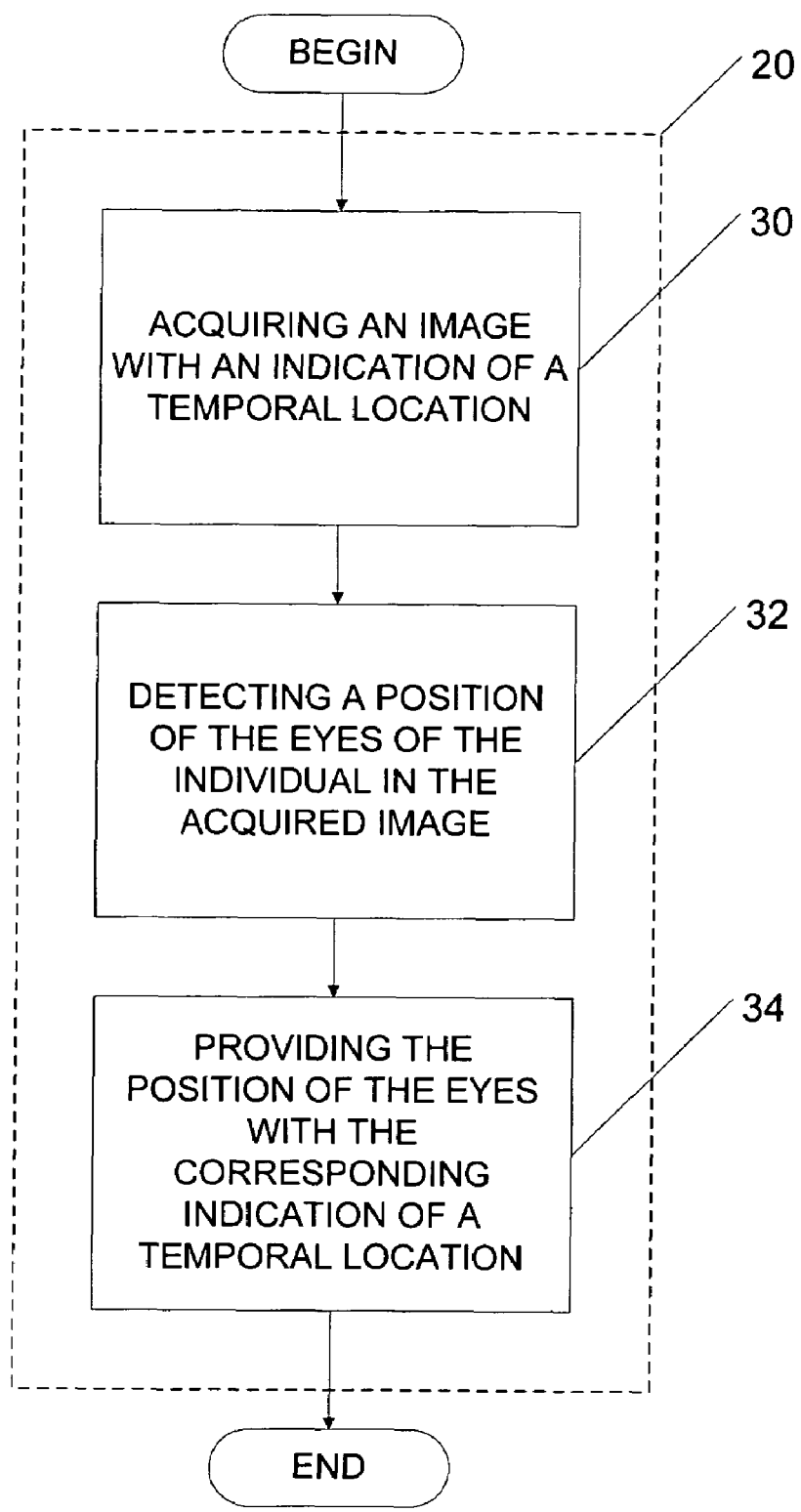
FIG. 3 is a flowchart showing how a plurality of gaze directions of an individual is acquired.

Now referring to FIG. 3, there is shown how the plurality of gaze directions of the individual is acquired.

According to step 30, an image is acquired with an indication of a temporal location. The image is acquired using the image acquisition unit 10. As explained above, the image acquired is preferably the resulting image from a subtraction of a bright image (in which the pupil of an eye will be white) of the individual from a dark image of the individual (in which the pupil of the eye of the individual will be black). The skilled addressee will appreciate that this is of great advantage in order to locate the pupil of the eye.

According to step 32, the position of the eyes, relative to the individual's head is detected in the acquired image. The position of the eyes of the individual is detected by the processing unit 12. More precisely, the position of the eyes is detected using a Kalman algorithm for detecting the pupil of the eye as disclosed in "Lips and face real time tracker", Conference on computer vision and pattern recognition, by Olivier, Pentland and Berard in Puerto Rico, June 1997, pp 123-129, which is hereby enclosed by reference. It should be appreciated that upon detection of the position of the eyes, an X coordinate and a Y coordinate are associated to each eye for identifying uniquely the position of each eye.

According to step 34, the position of the eyes is provided with the corresponding indication of a temporal location. The position of the eyes is provided in a memory not shown in FIG. 1.

Referring back to FIG. 2 and according to step 22, the acquired plurality of gaze directions of the individual is analyzed to provide a gaze pattern.

Figure 4:
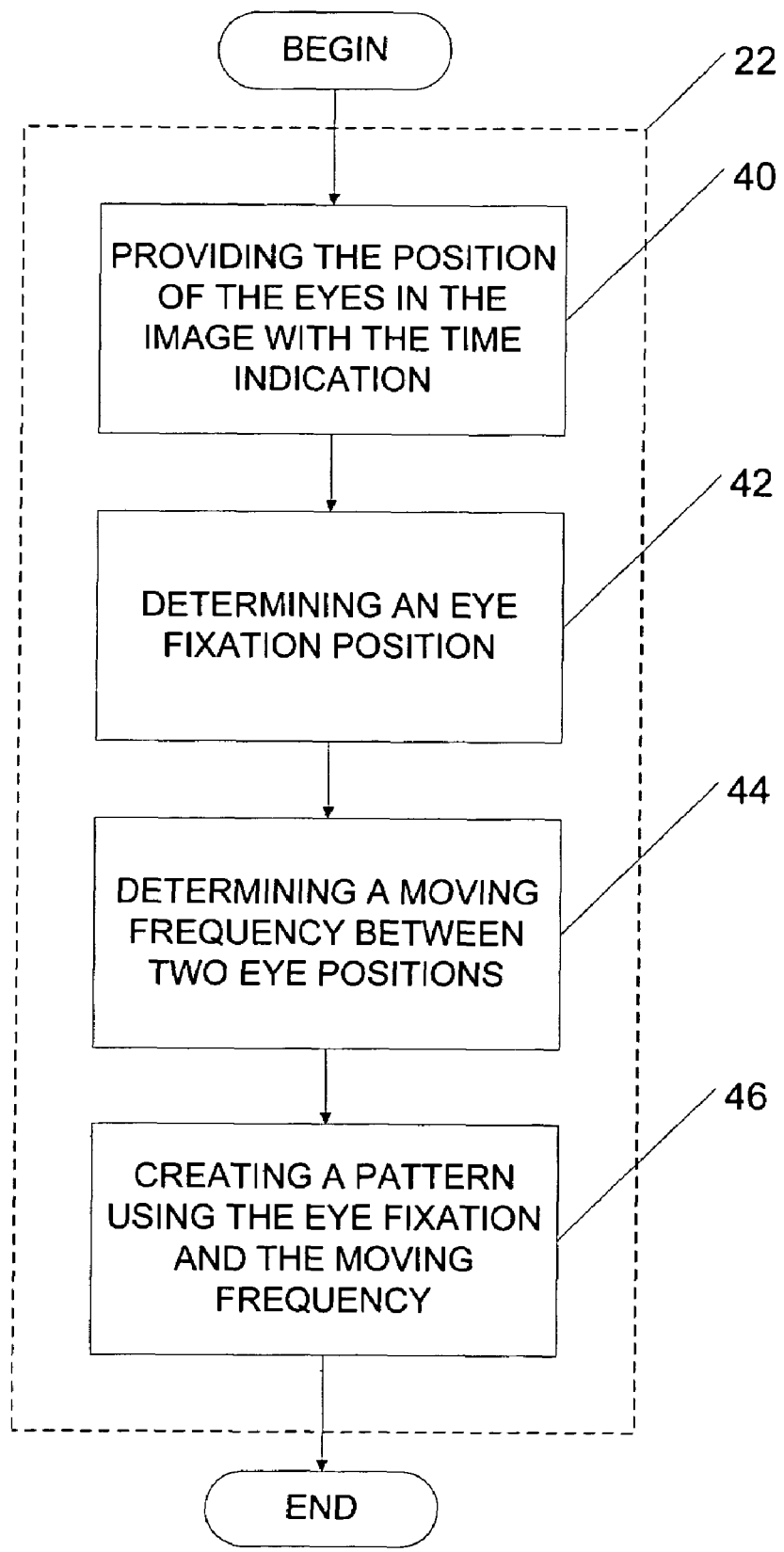
FIG. 4 is a flowchart showing how the plurality of gaze directions of the individual is analyzed in order to provide a gaze pattern.

Now referring to FIG. 4, there is shown how the acquired plurality of gaze directions of the individual is analyzed.

According to step 40, the position of the eyes in the image is provided with the time indication.

According to step 42, an eye fixation position is determined using the position of the eyes and the time indication. The eye fixation position is determined using the processing unit 12.

According to step 44, a moving frequency between two eye positions is determined using the processing unit 12.

According to step 46, a gaze pattern is created using the determined eye fixation and the determined moving frequency.

Referring back to FIG. 2 and according to step 24, an indication of a level of vigilance is generated using the created gaze pattern.

Figure 5:
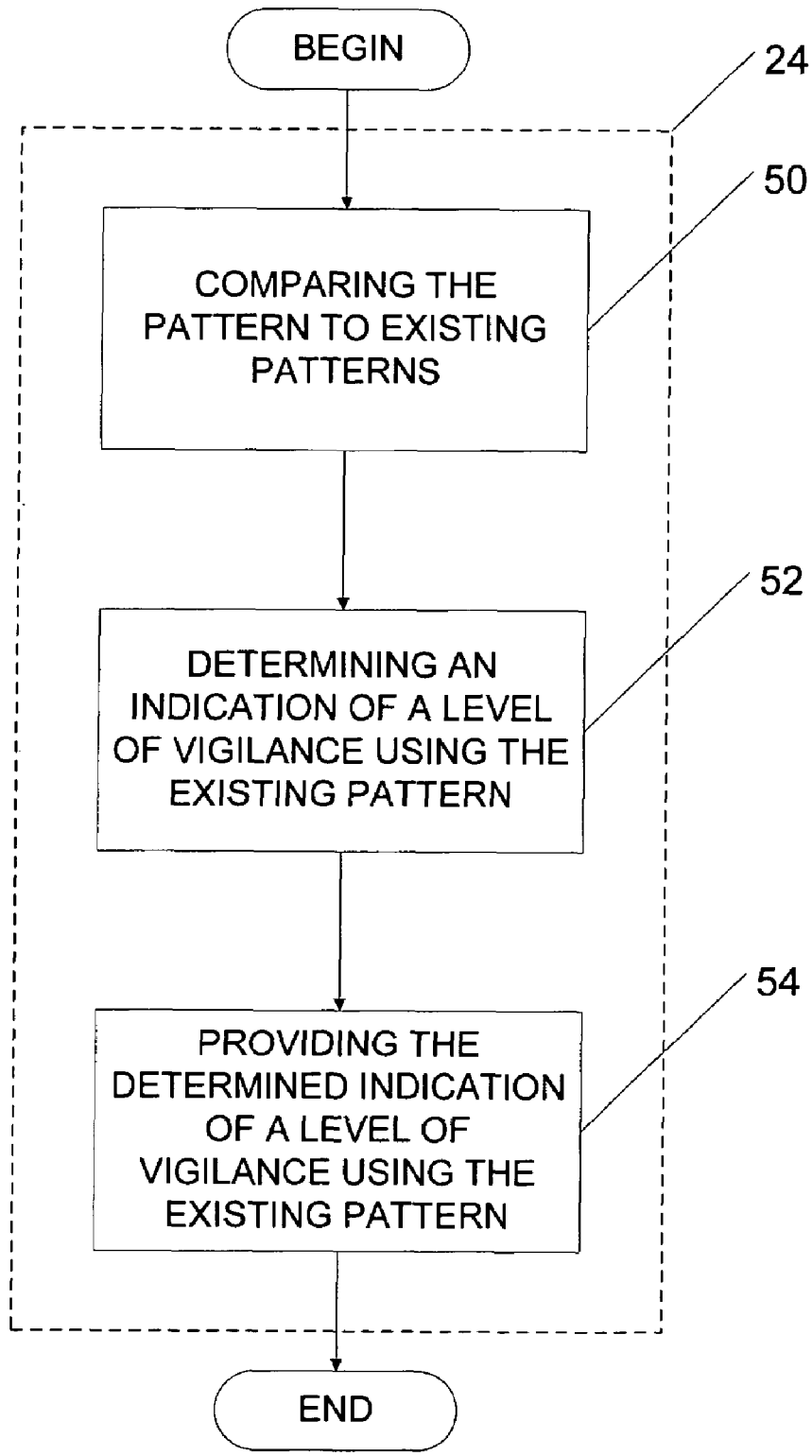
FIG. 5 is a flowchart showing how an indication of a level of vigilance is generated using the pattern.

Now referring to FIG. 5, there is shown how the indication of a level of vigilance is generated using the created pattern.

According to step 50, the created pattern is compared to existing patterns. It should be appreciated that a plurality of existing patterns is stored in the memory unit 18. Each existing patterns is related to a level of vigilance. In fact, it has been contemplated that in the case where a decrease of the level of vigilance of the individual occurs, the amount of alpha frequencies (which may be measured using an EEG) increase, the eye fixation position is concentrated roughly in one point and a reduction in saccade length is observed. Moreover, the eyes fixation positions become more structured, the frequency of the eye fixation decreases while the duration of an eye fixation position increases. It is therefore possible to relate a level of vigilance of the individual to a workload allocated to the individual and further to the gaze pattern of the individual.

According to step 52, an indication of a level of vigilance is determined using the result of the comparison of the gaze pattern of the individual with the plurality of existing patterns. The indication of a level of vigilance is determined using the processing unit 12. More precisely, the level of vigilance is selected using the corresponding level of vigilance for each of the existing patterns which are found to be close, as a result to the comparison performed in step 50, to the existing pattern for the individual. An interpolation may be performed using more than one corresponding level of vigilance.

While it has been disclosed that an indication of a level of vigilance for the individual is provided, it should be also understood by the skilled addressee that an indication of a variation of the level of vigilance for the individual may also be provided. Also the skilled addressee will appreciate that the indication of a level vigilance is preferably provided together with an indication of a corresponding temporal location which is not shown in FIG. 1 for clarity purposes.

According to step 54, the determined indication of a level of vigilance is provided to the data providing unit. It should be also understood that the determined indication of a level of vigilance may also be provided to the memory unit 18 with a corresponding gaze data stream pattern.

Referring back to FIG. 2 and according to step 26, an action is performed according to the generated indication of a level of vigilance. The action depends on various criteria such as an application sought, a level of vigilance, a variation in the level of vigilance, etc. For instance, a first given threshold may be provided for a level of vigilance or a second given threshold may be provided for a variation of the level of vigilance. In such case, an information signal may be provided in the case where the variation in the level of vigilance reaches the second given threshold or when the indication of a level of vigilance becomes lower than the first given threshold. The information signal may comprise an alarm signal.

The action is performed via the user interface 16 of the individual. Alternatively, the action may be performed at a remote location.

In an alternative embodiment, the apparatus for generating an indication of a level of vigilance of the individual comprises a gaze acquisition unit providing a gaze data stream of at least one eye of said individual, a processing unit receiving and using the provided gaze data stream to generate an indication of the level of vigilance and a data providing unit receiving and providing the indication of the level of vigilance. The gaze acquisition unit is preferably a image acquisition unit. In one embodiment, the processing unit is using the received gaze data stream over time with a formulae in order to generate the indication of the level of vigilance. Such formulae is disclosed in "A new method for describing search patterns and quantifying visual load using eye movement data" by Chia-Fen Chi and Fang-Tsan Lin, International Journal of Industrial Ergonomics 19 (1997) 249-257, hereby incorporated by reference.

The skilled addressee will appreciate that the embodiments disclosed may be used in many applications where monitoring the level of vigilance of an individual is critical, such as for instance in the case where the individual is the operator of a moving vessel, in the case where the individual is the operator of a factory, in the case where the individual is the operator of a power plant or the like.

Moreover, the skilled addressee will appreciate that such method and apparatus enable the detection of early stages of drowsiness (sleep stages); i.e., enable the prediction of drowsiness. Enabling such prediction is of great advantage as proper measures may be implemented in order to avoid potential fatal errors that may happen in later stages of drowsiness. The method and apparatus may also be used in order to monitor an evolution in time of a level of vigilance and may therefore be used in order to provide an information indicative of remaining cognitive resources of the individual. The information indicative of the remaining cognitive resources may then be related to an indication of a risk of incident/accident. It should be then understood that various alert signals may then be provided to the individual. It may be possible for instance to provide a customized test to the individual in order to assess his cognitive capabilities. The individual may also receive information/suggestions suitable to the indication of vigilance such as stopping a car for instance. Also an operator may also receive the information concerning the individual in order take necessary measures at a larger scale.

While it has been disclosed that the data providing unit 14 provides a detection signal to the user interface 16, it should be understood that the detection signal may be provided to a remote location using at least one of a body area network (BAN), a local area network (LAN), a metropolitan area network (MAN) and a wide area network (WAN).

The embodiments of the invention described above are intended to be exemplary only. The scope of the invention is therefore intended to be limited solely by the scope of the appended claims.

I claim:

1. A method for determining a level of vigilance of an individual, the method comprising:
   acquiring a plurality of timely-spaced images of at least one eye of the individual over a given time period;
   determining pupil positions of said at least one eye relative to a head of said individual at a plurality of instances in time;
   extracting eye fixation positions over time and a moving frequency between the eye fixation positions from said pupil positions;
   generating a gaze pattern indicative of a variation of the eye fixation positions over time;
   comparing said gaze pattern to existing patterns, each one of said existing patterns being associated to a given level of vigilance; and
   selecting a corresponding level of vigilance for said gaze pattern.

2. The method as claimed in claim 1, wherein said generating of said gaze pattern comprises using a given formulae over time for calculating said variation over time.

3. The method as claimed in claim 1, further comprising providing an information signal if said level of vigilance selected is lower than a given threshold.

4. The method as claimed in claim 3, wherein said information signal comprises an alarm signal.

5. The method as claimed in claim 1, wherein at least two consecutive levels of vigilance are selected over the given time period, and further comprising providing an indication of a variation between said at least two levels of vigilance.

6. The method as claimed in claim 5, further comprising providing an information signal if said variation exceeds a given threshold.

7. The method as claimed in claim 6, wherein said information signal comprises an alarm signal.

8. The method as claimed in claim 1, further comprising storing said level of vigilance selected with said gaze pattern generated.

9. The method as claimed in claim 1, wherein a corresponding black image and a corresponding white image are generated for each of said plurality of timely-spaced images, and further wherein said determining of said pupil positions of said at least one eye relative to said head of said individual comprises subtracting said corresponding white image to said corresponding black image.

10. The method as claimed in claim 1 wherein said comparing said gaze pattern to said existing patterns comprises performing an interpolation using more than one corresponding level of vigilance.

* * * * *